US009808235B2

United States Patent
Mayer et al.

(10) Patent No.: US 9,808,235 B2
(45) Date of Patent: Nov. 7, 2017

(54) DEVICE AND METHOD FOR FIXATING A SUTURE ANCHOR WITH A SUTURE OR A HEADED ANCHOR IN HARD TISSUE

(71) Applicant: Sportwelding GmbH, Schlieren (CH)

(72) Inventors: Jorg Mayer, Niederlenz (CH); Mario Lehmann, Les Pommerats (CH)

(73) Assignee: SPORTWELDING GMBH, Schlieren (CH)

( * ) Notice: Subject to any disclaimer, the term of this patent is extended or adjusted under 35 U.S.C. 154(b) by 299 days.

(21) Appl. No.: 14/467,411

(22) Filed: Aug. 25, 2014

(65) Prior Publication Data

US 2014/0364908 A1   Dec. 11, 2014

Related U.S. Application Data

(62) Division of application No. 13/358,798, filed on Jan. 26, 2012, now Pat. No. 8,834,542.

(60) Provisional application No. 61/437,227, filed on Jan. 28, 2011.

(51) Int. Cl.
*A61B 17/04* (2006.01)
*A61B 17/00* (2006.01)

(52) U.S. Cl.
CPC ...... *A61B 17/0401* (2013.01); *A61B 2017/00955* (2013.01); *A61B 2017/042* (2013.01); *A61B 2017/0409* (2013.01); *A61B 2017/0414* (2013.01); *A61B 2017/0458* (2013.01); *A61B 2017/0464* (2013.01); *F04C 2270/0421* (2013.01)

(58) Field of Classification Search
CPC .................................. A61B 17/0401
See application file for complete search history.

(56) References Cited

U.S. PATENT DOCUMENTS

| | | | |
|---|---|---|---|
| 5,464,427 A | 11/1995 | Curtis et al. | |
| 5,522,844 A | 6/1996 | Johnson | |
| 5,709,708 A | 1/1998 | Thal | |
| 5,733,307 A | 3/1998 | Dinsdale | |
| 5,891,168 A | 4/1999 | Thal | |
| 5,993,458 A | 11/1999 | Vaitekunas et al. | |
| 6,024,758 A | 2/2000 | Thal | |
| 6,214,031 B1 | 4/2001 | Schmieding et al. | |

(Continued)

FOREIGN PATENT DOCUMENTS

DE   112011102287   5/2013
EP      2221014      8/2010

(Continued)

*Primary Examiner* — Andrew Yang
(74) *Attorney, Agent, or Firm* — Rankin, Hill & Clark LLP

(57) ABSTRACT

A device and method for fixating soft tissue to hard tissue with the aid of a suture anchor and a suture or with the aid of a headed anchor, wherein the anchor is forced into the hard tissue and then anchored therein by in situ liquefaction of a material having thermoplastic properties. The device includes a vibration tool and the anchor and possibly a support element, wherein the anchor includes an anchor foot and a thermoplastic sleeve. The thermoplastic sleeve includes the material having thermoplastic properties. The anchor foot has a distal end suitable for being forced into hard tissue and it is connected to the distal end of the vibration tool and the thermoplastic sleeve sits on a proximal face of the anchor foot, the vibration tool and/or a proximal portion of the anchor foot extending into or through the thermoplastic sleeve.

18 Claims, 5 Drawing Sheets

(56) References Cited

U.S. PATENT DOCUMENTS

| | | |
|---|---|---|
| 6,319,270 B1 | 11/2001 | Grafton et al. |
| 6,508,830 B2 | 1/2003 | Steiner |
| 6,511,499 B2 | 1/2003 | Schmieding et al. |
| 6,517,564 B1 | 2/2003 | Grafton et al. |
| 6,544,281 B2 | 4/2003 | ElAttrache et al. |
| 6,569,188 B2 | 5/2003 | Grafton et al. |
| 6,620,185 B1 | 9/2003 | Harvie et al. |
| 6,641,597 B2 | 11/2003 | Burkhart et al. |
| 7,008,226 B2 | 3/2006 | Mayer et al. |
| 7,172,420 B2 | 2/2007 | Huguenin et al. |
| 7,211,088 B2 | 5/2007 | Grafton et al. |
| 7,226,469 B2 | 6/2007 | Benavitz et al. |
| 7,329,272 B2 | 2/2008 | Burkhart et al. |
| 7,335,205 B2 | 2/2008 | Aeschlimann et al. |
| 7,442,202 B2 | 10/2008 | Dreyfuss |
| 7,678,134 B2 | 3/2010 | Schmieding et al. |
| 7,695,495 B2 | 4/2010 | Dreyfuss |
| 7,785,347 B2 | 8/2010 | Harvie et al. |
| 2004/0038180 A1 | 2/2004 | Mayer et al. |
| 2004/0068267 A1 | 4/2004 | Harvie et al. |
| 2005/0222575 A1 | 10/2005 | Ciccone |
| 2005/0222618 A1 | 10/2005 | Dreyfuss et al. |
| 2005/0222619 A1 | 10/2005 | Dreyfuss et al. |
| 2006/0105295 A1 | 5/2006 | Mayer et al. |
| 2006/0161159 A1 | 7/2006 | Dreyfuss et al. |
| 2007/0060922 A1 | 3/2007 | Dreyfuss |
| 2007/0073299 A1 | 3/2007 | Dreyfuss |
| 2007/0288027 A1 | 12/2007 | Grafton et al. |
| 2008/0109038 A1 | 5/2008 | Steiner et al. |
| 2008/0109080 A1 | 5/2008 | Aeschlimann et al. |
| 2008/0208253 A1 | 8/2008 | Dreyfuss et al. |
| 2009/0131947 A1 | 5/2009 | Aeschlimann et al. |
| 2009/0138053 A1 | 5/2009 | Assell et al. |
| 2009/0171394 A1 | 7/2009 | Abdou |
| 2009/0187216 A1 | 7/2009 | Schmieding et al. |
| 2009/0192546 A1 | 7/2009 | Schmieding et al. |
| 2009/0204152 A1 | 8/2009 | Blain |
| 2009/0264928 A1 | 10/2009 | Blain |
| 2010/0023057 A1 | 1/2010 | Aeschlimann et al. |
| 2010/0217266 A1 | 8/2010 | Helevirta et al. |
| 2010/0262186 A1 | 10/2010 | Sodeika et al. |
| 2011/0112576 A1 | 5/2011 | Nguyen |
| 2012/0179200 A1 | 7/2012 | Cauldwell |
| 2012/0191142 A1 | 7/2012 | Bouduban |
| 2012/0239085 A1 | 9/2012 | Schlotterback |
| 2012/0245631 A1 | 9/2012 | Lunn |
| 2012/0245634 A1 | 9/2012 | Kaplan |
| 2012/0330327 A1 | 12/2012 | McClellan |
| 2013/0006276 A1 | 1/2013 | Lantz |
| 2013/0006320 A1 | 1/2013 | Hintz |
| 2013/0023930 A1 | 1/2013 | Stone |
| 2013/0035721 A1 | 2/2013 | Brunelle |
| 2013/0046340 A1 | 2/2013 | Huxel |
| 2013/0072976 A1 | 3/2013 | Van Der Burg |
| 2013/0079818 A1 | 3/2013 | Lizardi |
| 2013/0096611 A1 | 4/2013 | Sullivan |
| 2013/0123848 A1 | 5/2013 | Duggal |
| 2013/0138123 A1 | 5/2013 | Stone |
| 2013/0138152 A1 | 5/2013 | Stone |
| 2013/0144334 A1 | 6/2013 | Bouduban |
| 2013/0144343 A1 | 6/2013 | Arnett |

FOREIGN PATENT DOCUMENTS

| | | |
|---|---|---|
| EP | 2486856 | 8/2012 |
| EP | 2537470 | 12/2012 |
| EP | 2596764 | 5/2013 |
| WO | 2008/128367 | 10/2008 |
| WO | 2008/131884 | 11/2008 |
| WO | 2009/055952 | 5/2009 |
| WO | 2009/109057 | 9/2009 |
| WO | 2009/132472 | 11/2009 |
| WO | 2010/045751 | 4/2010 |
| WO | 2010/117982 | 10/2010 |
| WO | 2011/119684 | 9/2011 |
| WO | 2011/133233 | 10/2011 |
| WO | 2011/140486 | 11/2011 |
| WO | 2012006161 | 1/2012 |
| WO | 2012/030754 | 3/2012 |
| WO | 2012/036889 | 3/2012 |

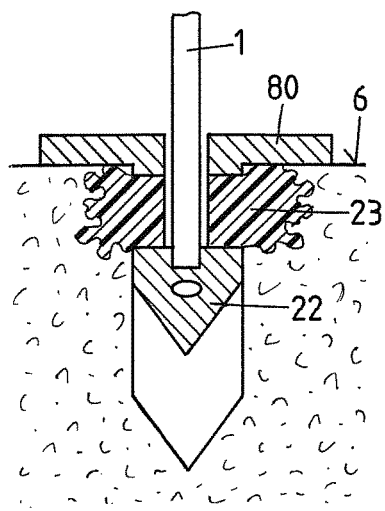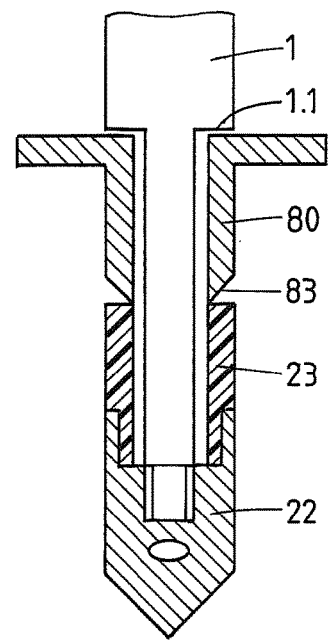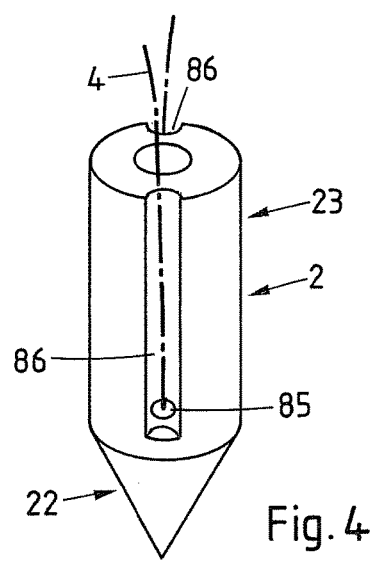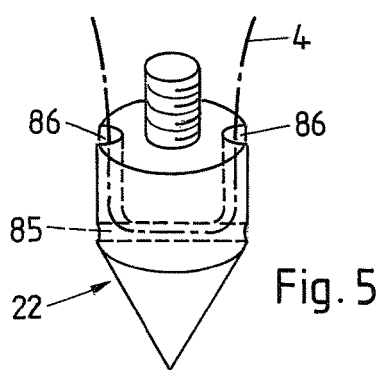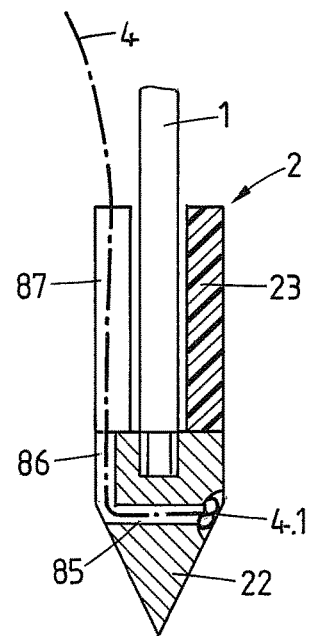
Fig. 2
Fig. 3
Fig. 4
Fig. 5
Fig. 6

DEVICE AND METHOD FOR FIXATING A SUTURE ANCHOR WITH A SUTURE OR A HEADED ANCHOR IN HARD TISSUE

BACKGROUND OF THE INVENTION

Field of the Invention

The invention is in the field of medical technology and concerns a device and a method for fixating a suture anchor with a suture or a headed anchor in hard tissue, in particular for attaching, with the aid of the suture or the headed anchor, soft tissue to the hard tissue, wherein the hard tissue is in particular bone tissue of a human or animal patient, but may also be e.g. augmented bone tissue or a bone substitute.

Description of Related Art

The publication WO 2009/109057 (Woodwelding) discloses devices and methods for attaching a suture to hard tissue with the aid of a suture anchor, wherein the suture anchor comprises a material having thermoplastic properties and is anchored in a hard tissue opening with the aid of vibratory energy used for in situ liquefaction of the material having thermoplastic properties. The liquefied material penetrates into pores or other suitable structures of the hard tissue in the hard tissue opening, where on re-solidification it constitutes a positive fit connection between the hard tissue and the suture anchor. The devices as disclosed in the named publication comprise a vibration source in a housing, a vibration tool, a guide tube, the anchor, the suture and possibly a pushing bush. The proximal end of the vibration tool is coupled to the vibration source, the proximal end of the guide tube is supported on the housing, the anchor is arranged at the distal end of the vibration tool. The anchor comprises the material having thermoplastic properties in the form of a thermoplastic sleeve, the anchor or the vibration tool reaching through the sleeve and the sleeve being clamped between a foot piece of the anchor and the vibration tool, the guide tube or the pushing bush. A suture loop is held in the foot piece of the anchor, two suture end sections extending through further parts of the anchor and through portions of the vibrating tool and the guide tube from where they exit to possibly be kept straightened or tensioned by being attached to the guide tube or the housing or a suture management system.

For implantation, an opening is provided in the hard tissue and the distal end of the device or the suture anchor respectively is introduced into the opening, such that at least part of the thermoplastic sleeve is located in the opening, wherein a cross section of the opening is slightly larger than the cross section of the thermoplastic sleeve such that the material having thermoplastic properties is located near the hard tissue of the wall of the opening, but such that, on introducing the anchor into the opening, there is no friction between the sleeve and the wall of the opening. The vibration source is then activated and the material having thermoplastic properties of the thermoplastic sleeve being clamped between a vibrating element (vibration tool or anchor foot being coupled to the vibration tool) and a counter element (anchor foot not being coupled to the vibration tool, guide tube or pushing bush) is liquefied starting from its proximal and/or distal face and flows into the hard tissue, whereby the thermoplastic sleeve gets shorter. For maintaining the clamping force on the thermoplastic sleeve while the latter is getting shorter, device elements are moved relative to each other in an axial direction which is preferably effected by a pre-tensioned spring arranged together with at least the thermoplastic sleeve and the elements between which the thermoplastic sleeve is clamped in a closed load frame. This measure allows automatic anchoring of the suture anchor, the surgeon only having to position the device with the distal end of the guide tube on the surface of the hard tissue and to activate the vibration source. However, special measures are needed for allowing checking and tuning of the device before the anchoring process, without liquefaction of the material of the thermoplastic sleeve.

The publication US 2009/131947 (Woodwelding) also discloses a method for attaching a suture to hard tissue with the aid of a suture anchor comprising a thermoplastic material which is liquefied in situ with the aid of vibratory energy. The disclosed method is based on the same principle as the method which is briefly described above, wherein the suture is threaded through a distal end portion of the anchor, wherein a proximal end portion of the anchor comprises the thermoplastic material, and wherein a proximal face of the anchor is held against a distal face of a vibrating tool by pulling suture end portions in a proximal direction.

Further methods and devices for attaching sutures to hard tissue with the aid of suture anchors are disclosed in the publications U.S. Pat. No. 7,678,134, U.S. Pat. No. 7,695,495, US-2006/161159, US-2009/192546, US-2009/187216 (all to Arthrex), U.S. Pat. No. 5,733,307 (Dinsdale), or U.S. Pat. No. 6,508,830 (Steiner), wherein the disclosed anchors comprise an interference screw to be screwed into a bone opening provided for the purpose or a plug preferably made of bone material and to be press-fitted into a bone opening provided for the purpose, wherein the suture is either held by the screw or plug or by an additional element being retained in the opening with the aid of the screw or plug.

Methods of anchoring an item in an opening provided in hard tissue, e.g. in bone tissue of a human or animal patient with the aid of a material having thermoplastic properties which is liquefied in situ and made to penetrate the hard tissue of the wall of the opening are disclosed in the publications U.S. Pat. No. 7,335,205, U.S. Pat. No. 7,008,226, US-2006/0105295, US-2008/109080, US-2009/131947, WO-2009/109057, and WO-2009/132472. The disclosure of all the named publications and applications is enclosed herein by reference.

BRIEF SUMMARY OF THE INVENTION

Generally speaking, it is the object of the invention to create a further method and a further device for fixating a suture anchor with a suture or a headed anchor in hard tissue of a human or animal patient, wherein the suture fixated to the hard tissue with the aid of the suture anchor, or the headed anchor are to be, in particular, suitable for attaching soft tissue to the hard tissue, wherein the hard tissue is in particular bone tissue, but may also be e.g. augmented bone tissue or a bone substitute, and wherein one of the method steps comprises in situ liquefaction of a material having thermoplastic properties and bringing the liquefied material into contact with the hard tissue. The suture anchor or the headed anchor is fixated in a hard tissue opening by penetration of the liquefied material into hard tissue walls of the opening (trabecular structure of the tissue or preferably undercut cavities specially provided for the anchorage) or it is fixated beyond a hard tissue opening by the liquefied material expanding beyond the opening, i.e. on a non-accessible side of a hard tissue layer, possibly combined with penetrating the hard tissue surface on this non-accessible side of a hard tissue layer. On re-solidification the material which penetrated into the hard tissue constitutes a positive fit connection between this hard tissue and the anchor; on re-solidification the material expanded beyond the hard tissue opening constitutes a body which cannot pass the opening. The improvement achieved by the invention as compared with state of the art methods and devices serving the same purpose concern in particular the simplicity of method and device and/or the strength of the fixation in the hard tissue of the suture or the suture anchor or of the headed anchor.

It is the object of the invention to create a further device and a further method for fixating a suture anchor or a headed anchor in or beyond a hard tissue opening, wherein the anchor is anchored in the opening with the aid of a material having thermoplastic properties which is liquefied in situ and brought into contact with the hard tissue, in particular made to penetrate the hard tissue of the wall of the hard tissue opening, and wherein it is to be possible to effect the step of providing the hard tissue opening or part thereof and the step of anchoring the anchor with the aid of the same instruments and without moving the instruments away from the fixation site between the two steps. Device and method according to the invention are to be suitable, in particular, for minimally invasive surgery, but are to be applicable in open surgery also.

According to the invention, the suture anchor or the headed anchor comprises a distal end equipped for being forced into hard tissue substantially without providing an opening therein. The anchor is forced into the hard tissue in an initial forcing step and is then fixated in or beyond the opening with the aid of a material having thermoplastic properties and being liquefied in situ to be brought into contact with the hard tissue, in particular to penetrate the hard tissue of the wall of the opening (anchoring step). Therein a vibration tool used in the anchoring procedure, i.e. for the in situ liquefaction of the material having thermoplastic properties is also used for the forcing of the anchor into the hard tissue, wherein such forcing is preferably enhanced by vibration.

The anchor comprises an anchor foot and a thermoplastic sleeve sitting on the anchor foot and comprising the material having thermoplastic properties. The vibration tool and/or the anchor foot extends through the thermoplastic sleeve, the distal end of the vibration tool being attached to the anchor foot. The vibration tool and its connection to the anchor foot are designed for being able to transmit to the anchor foot the forces necessary for the forcing step (pushing force) and for the anchoring step (pulling force) and vibration, preferably for both steps. The tool is therefore attached to the anchor foot in a way suitable for transmission of compressive and tensile forces and of mechanical vibration and in a way to be easily separated from the anchor foot after completion of the two-step process (forcing step and anchoring step).

For the forcing step and for the anchoring step, the vibration tool is coupled to a vibration source, in particular to a source of ultrasonic vibration (e.g. piezoelectric vibration generator, possibly comprising a booster to which the tool is coupled) and the assembly of tool and anchor foot (or anchor) is suitable for transmission of the vibration from the proximal tool end to the anchor foot or anchor, preferably such that a proximal anchor face vibrates with a maximal longitudinal amplitude. The material to be liquefied in the anchoring step is arranged in the vicinity of this vibrating anchor face. It is possible also to activate the tool to vibrate in a radial or in a rotational direction.

Suitable in situ liquefaction of a material having thermoplastic properties with the aid of vibration energy combined with an acceptable thermal loading of the tissue and suitable mechanical properties of the positive fit connection to be produced is achievable by using materials with thermoplastic properties having an initial modulus of elasticity of at least 0.5 GPa and a melting temperature of up to about 350° C. in combination with vibration frequencies preferably in the range of between 2 and 200 kHz (preferably 15 to 40 kHz, or even more preferably between 20 and 30 kHz or for liquefaction in direct contact with the vibrating tool between 25 and 35 kHz). The modulus of elasticity of at least 0.5 GPa is in particular necessary if the material having thermoplastic properties is to transmit the vibration without loss of mechanical stiffness. If the material having thermoplastic properties is not to transmit the vibration, but is to be liquefied where it is in direct contact with the vibrating tool or if the material having thermoplastic properties is to transmit the vibration but is supported and guided by device parts of other materials, the material having thermoplastic properties may have a somewhat smaller modulus of elasticity.

For the anchoring step, it is preferable to work with a substantially constant output of vibrational power, i.e. with vibration (base vibration) of substantially constant frequency and amplitude, wherein the frequency is in the above named frequency range and is a resonant frequency of the vibrating system, and wherein the amplitude is in the range of 10 to 50 μm, preferably 20-40 μm. For the forcing step, in particular in cases in which the hard tissue constitutes a relatively high resistance, vibrational modes as known from e.g. vibration assisted bone cutting are preferable. Such vibration modes usually comprise pulses of higher amplitude and possibly sharper profiles (e.g. rectangular profile or Dirac impulse) and are e.g. provided by modulating the amplitude of the base vibration to e.g. form pulses of higher amplitude and preferably by also sharpening the input wave form as compared with the base vibration and by matching the system's resonance frequency. The so created pulses can comprise one or several wave cycles of the base vibration each, and can be periodic with a modulation frequency preferably in the range of 0.5-5 kHz or they can be generated stochastically (in amplitude and modulation frequency) but in any case in phase with the system's resonance frequency. A means for producing stochastically occurring pulses is e.g. described in the publication U.S. Pat. No. 7,172,420 (St. Imier). Therein the higher amplitude of the pulses is preferably greater than the base vibration amplitude by a factor of between 2 and 10.

Alternatively, such pulses can be achieved by overlaying the base vibration or replacing it with a pulse excitation generated by a mechanical impulse generator (e.g. comprising a rotationally driven unbalanced mass or hammer). Therein the higher amplitude of the pulses is preferably again greater than the base vibration amplitude by a factor of between 2 and 10 and the pulse frequency which may be regular in the region of 20 to 200 Hz and in particular lower than the lowest resonance frequency of the vibrating system (e.g. undesired flexural vibration of the sonotrode). The low pulse frequencies are particularly important if material liquefaction during the forcing step is possible, but is to be prevented as best as possible.

If as described above two different vibration modes are to be used in the forcing and in the anchoring step, the vibration source to which the vibration tool is coupled during the two steps is to be equipped for selectively producing the two vibration modes and with switching means for switching the vibration source from one vibration mode into the other one.

Materials having thermoplastic properties suitable for the thermoplastic sleeve of the device and the method according to the invention are thermoplastic polymers, e.g.: resorbable or degradable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable or non-degradable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonate-urethane (e.g. Bionate by DSM, in particular types 65D and 75D). An overview table of polymers and applications is listed in Wintermantel, page 150; specific examples can be found in Wintermantel page 161 if. (PE, Hostalen Gur 812, Hochst AG), pages 164 if. (PET) 169ff. (PA, namely PA 6 and PA 66), 171 if. (PTFE), 173 if. (PMMA), 180 (PUR, see table), 186 if. (PEEK), 189 if. (PSU), 191 if (POM—Polyacetal, tradenames Delrin, Tenac, has also been used in endoprostheses by Protec).

The material having thermoplastic properties may further contain foreign phases or compounds serving further functions. In particular, the thermoplastic material may be strengthened by admixed fibers or whiskers (e.g. of calcium phosphate ceramics or glasses) and such represent a composite material. The material having thermoplastic properties may further contain components which expand or dissolve (create pores) in situ (e.g. polyesters, polysaccharides, hydrogels, sodium phosphates), compounds which render the implant opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

Fillers used may include degradable, osseostimulative fillers to be used in degradable polymers, including: β-Tricalciumphosphate (TCP), Hydroxyapatite (HA, <90% crystallinity); or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see SM Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 µm (contents, preferentially 10-25% by volume), sub-micron (nanofillers as from precipitation, preferentially plate like aspect ratio >10, 10-50 nm, contents 0.5 to 5% by volume). Experiments show that liquefaction with the aid of ultrasonic vibration energy allows filling of the thermoplastic polymer to a relatively high degree without impairing the capability of the liquefied material to penetrate structures as e.g. the trabecular structure of viable cancellous bone.

Anchor portions other than the thermoplastic sleeve may consist of any suitable material (e.g. polymer, metal, ceramic, glass) which material may be bio-resorbable or not bio-resorbable and liquefiable or not liquefiable. Non-bioresorbable or non-biodegradable such materials may comprise surfaces equipped for furthering osseointegration (e.g. per se known surface structures or coatings) where in contact with the bone tissue, in particular if the material of the thermoplastic sleeve is bio-resorbable or bio-degradable and therefore the anchoring function needs to be gradually taken over by osseointegration. Good results have e.g. been achieved with anchor feet of polylactic acid (PLA) filled with Hydroxyapatite or calciumphosphates, in particular of PLLA filled with 60% tricalciumphosphate or PDLLA 70%/130% (70% L and 30% D/L) filled with 30% biphasic calciumphosphate, combined with thermoplastic sleeves of PLDLLA 70%/130% (70% L and 30% D/L), as available from Böhringer as LR706. The PDLLA 70%/30% filled with 30% of biphasic calciumphosphate and similar materials prove to be suitable also for the thermoplastic sleeve and therefore suitable for manufacturing bio-resorbable, one-piece anchors being made of one material only.

The distal end of the anchor foot or the anchor, which distal end is to be equipped for being forced into the hard tissue, needs to comprise a material having a corresponding mechanical strength which is dependent on the mechanical resistance expected of the hard tissue into which the anchor is to be forced. If such resistance is relatively high (forcing through cortical bone or hard and dense cancellous bone) the distal end of the anchor comprises e.g. a metal such as e.g. titanium or a titanium alloy, a ceramic material such as e.g. sintered calcium phosphate (e.g. hydroxyapatite) or engineering ceramics (e.g. zirkonia, alumina) or PEEK or a comparable high temperature resistant polymer, while other anchor portions are made e.g. of a biocomposite material such as e.g. the above mentioned filled polylactides or of one of the other above mentioned thermoplastic polymers. Alternatively such distal end of the anchor may comprise a hard and possibly abrasive coating e.g. made by plasma sprayed deposition of calcium phosphate or titanium powder on PEEK or polylactide or biocomposites. If the named resistance is smaller (forcing into cancellous bone), the distal end of the anchor foot may consist of a lesser material and may even consist of the same material having thermoplastic properties as the thermoplastic sleeve. In the latter case this material may even be partly liquefied during the forcing step at surfaces of the distal anchor end. Such liquefaction can be kept within acceptable limits if (a) vibration used for enhancing the forcing is of a relatively low frequency (<10 Khz), which even at high amplitudes can only cause very slow liquefaction, and if (b) the anchoring step is carried out immediately after the forcing step, i.e. before possibly liquefied material at the distal anchor end can lock the anchor foot relative to the hard tissue. If the mechanical strength of the hard tissue into which the anchor is to be forced is poor, the condition (b) is of little importance.

As the tools used for the fixation process can be designed very slim and 200 mm long or even longer, device and method according to the invention are in particular suitable for minimally invasive surgery but are also applicable in open surgery. The assembly of vibration tool and anchor foot or anchor preferably has a length between the proximal end and the proximal anchor face corresponding to a multiple of half of the vibration wavelength in the tool material (for a tool and an anchor foot made of titanium and a vibration frequency of 20 kHz, this length is preferably n times 126 mm, n being an integer).

For easy manufacturing not only the suture anchor or headed anchor, but also the axial channel through the thermoplastic sleeve and the distal end of the vibration tool will have a circular cross section. However this is not a condition for the invention, according to which any one of the named items may have a non-circular cross section, wherein the cross section of the anchor foot is preferably the same as the cross section of the thermoplastic sleeve or slightly larger than the latter.

Device and method according to the invention are applicable for all surgical procedures in a human or animal patient, in which surgical procedures a suture needs to be attached to hard tissue, in particular to bone tissue, wherein the fixation of the anchor is preferably achieved underneath the cortical bone layer (so called sub-cortical fixation in cancellous bone situated underneath the cortical bone layer, or on the inner side of the cortical bone layer, or in a cavity or soft tissue adjoining the cortical bone layer on its inner side). In the same manner, the device and the method according to the invention are applicable for attaching a suture to a replacement material (bone substitute material) having features comparable to the features of hard tissue, or to part hard tissue part replacement material or possibly even to a further implant (e.g. endoprosthesis).

Examples of such applications are:
regarding foot and ankle: lateral stabilization, medial stabilization, achilles tendon repair or reconstruction, hallux valgus repair or reconstruction or treatment, midfoot repair or reconstruction, metatarsal ligament repair or reconstruction, digital tendon transfers, peroneal retinaculum repair or reconstruction;
regarding the knee: medial collateral ligament repair or reconstruction, lateral collateral ligament repair or reconstruction, patellar tendon repair or reconstruction, posterior oblique ligament repair or reconstruction, iliotibial band tenodesis;
regarding hand and wrist: scapholunate ligament repair or reconstruction, carpal ligament repair or reconstruction, repair or reconstruction of collateral ligaments, ulnar collateral ligament repair or reconstruction, radial collateral ligament repair or reconstruction, repair or reconstruction of flexor and extensor tendons at the PIP, DIP and MCP joints for all digits, digital tendon transfers, capsular reattachment of the metacarpophalangeal joint;
regarding the elbow: biceps tendon reattachment, ulnar or radial collateral ligament repair or reconstruction;
regarding the hip: capsular repair or reconstruction, acetabular labral repair or reconstruction;
regarding the shoulder: rotator cuff repair or reconstruction, bankart repair or reconstruction, SLAP lesion repair or reconstruction, biceps tenodesis, acromioclavicular separation repair or reconstruction, deltoid repair or reconstruction, capsular shift or capsulolabral repair or reconstruction;
regarding the pelvis: bladder neck suspension for female urinary incontinence due to urethral hypermobility or intrinsic sphincter deficiency;
regarding veterinary surgery: reconstruction of the cranial cruciate ligament (ccl in dogs), capsular repair in the shoulder and hip, general fixation of ligaments and tendons to bone, especially in shoulder, hip, knee, elbow and paws.

BRIEF DESCRIPTION OF THE DRAWINGS

The invention is described in further detail in connection with the appended Figs., wherein:

FIG. 2 illustrates the method according to FIG. 1 but not applied for providing a sub-cortical fixation;

FIGS. 3 to 6 show further exemplary embodiments of anchors and devices suitable for the fixation methods as illustrated in FIGS. 1 and 2;

DETAILED DESCRIPTION OF THE INVENTION

The appended FIGS. 1 to 10 illustrate fixation of a suture anchor or a headed anchor in hard tissue (preferably bone tissue) according to the invention, i.e. in a forcing step and an anchoring step, as well as anchors and devices suitable for such fixation. In the anchoring step the anchor is anchored in the hard tissue by in situ liquefaction of a material having thermoplastic properties with the aid of vibrational energy and by making the liquefied material to penetrate into the hard tissue (trabecular tissue structure or specially provided, preferably undercut cavities) or into a cavity on a non-accessible side of the hard tissue. In the forcing step, which is preceding the anchoring step, the anchor is forced into the hard tissue thereby providing an opening in the hard tissue (or at least part thereof) in which or beyond which the anchor is to be anchored, wherein for such forcing substantially the same tools are used as in the anchoring step. Therein the anchor is forced into the hard tissue preferably assisted by vibration energy provided through the same vibration tool as used for the anchoring step. The principle of the anchoring step as used in the method according the invention and as illustrated in the figures is described for different applications in the publication US-2009/131947.

For being able to be forced into the hard tissue, the anchor or an anchor foot being part of the anchor respectively is made of a material having a suitable mechanical stability, e.g. of a metal such as titanium or a titanium alloy, and its distal face has a suitable shape, it is e.g. tapering, pointed or otherwise sharp. For being able to be forced through a cortical bone layer, the anchor foot is e.g. shaped like a bone awl. The distal face of the anchor foot may also be equipped as a punching tool (see FIG. 10) for vibration assisted punching as disclosed in the publication WO 2008/131884 (Stryker Trauma GmbH). Less effective anchor feet may be able to be forced into cancellous bone only, which means that a bone in which the anchor is to be fixated is to be decorticated or an opening is to be provided through the cortical bone layer before positioning the anchor and forcing it into the bone. It is possible also to provide a pilot bore in the bone tissue for safe positioning of the anchor, wherein the pilot bore is then enlarged regarding cross section and/or depth by the anchor being forced into the pilot bore. It is possible also to first position a K-wire and then force the anchor into the hard tissue using the K-wire as guide. For this purpose, the anchor and at least a distal end of the vibration tool needs an axial channel for accommodation of the K-wire.

Figure 1:
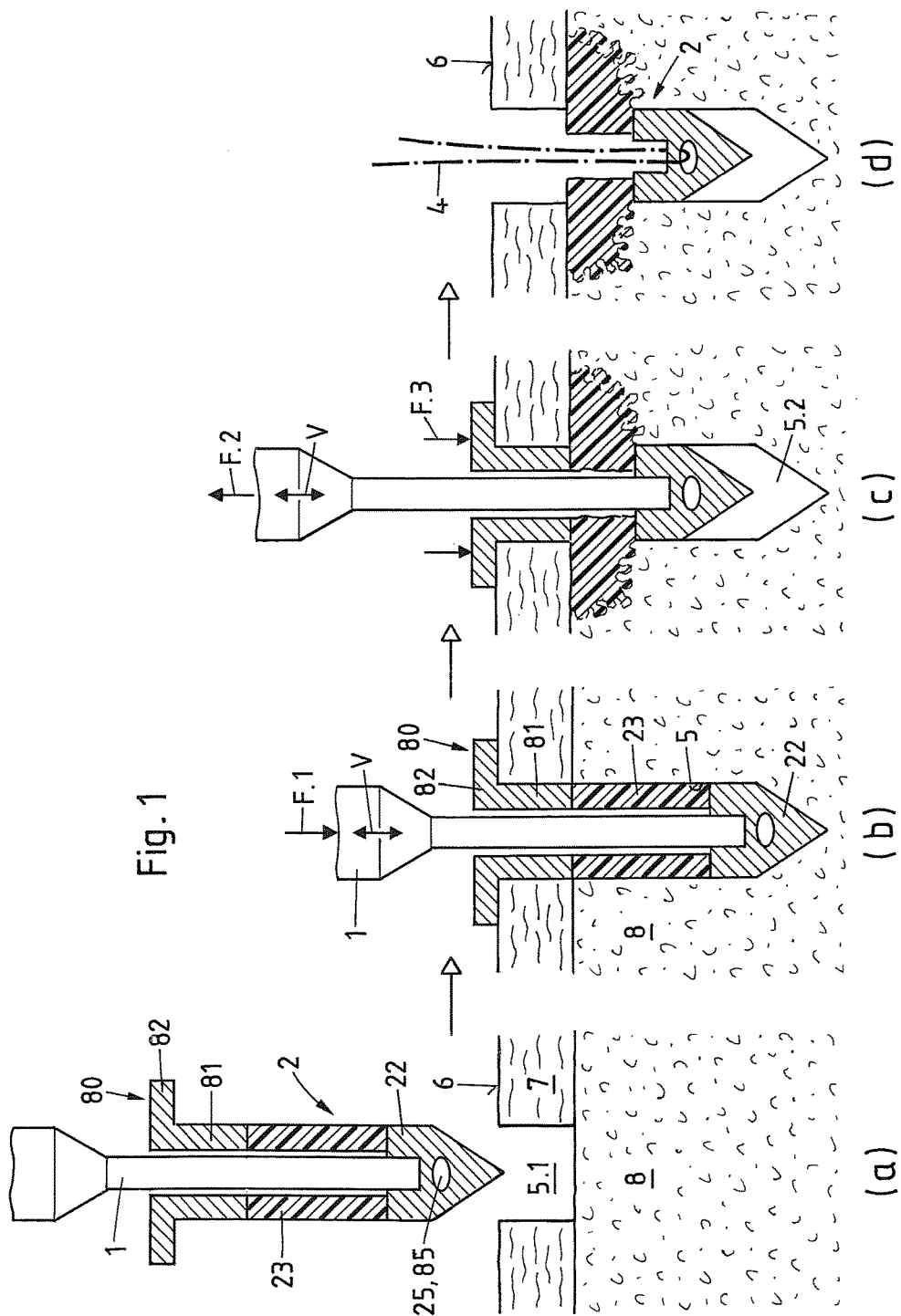
FIG. 1 illustrates a first exemplary embodiment of the anchor fixation according to the invention, wherein the fixation is a sub-cortical fixation for which the thermoplastic sleeve is liquefied preferably starting from its proximal end.

FIG. 1 illustrates an exemplary embodiment of the invention with four consecutive phases (a) to (d) of a first exemplary embodiment of the method according to the invention. Therein the suture anchor 2 is to be fixated in cancellous bone tissue 8 being situated underneath a cortical bone layer 7, wherein e.g. a blind opening 5.1 reaching through the cortical bone layer 8 only is provided beforehand. Of course a similar fixation can be achieved also if no cortical layer is present, wherein the fixation location will have a predefined depth and is situated e.g. underneath a denser layer of cancellous bone in cancellous bone of a lesser density. The suture anchor 2 is arranged on the distal end of a vibration tool 1, and it comprises an anchor foot 22 (distal anchor part) and a thermoplastic sleeve 23 (proximal anchor part), wherein the thermoplastic sleeve 23 comprises the material to be liquefied (material having thermoplastic properties) or is preferably made thereof, and wherein a loop of the suture 4 is held in a system 25 of passages and/or grooves (e.g. constituted, as illustrated, by a simple eyelet 85) provided in the anchor foot 22. For simplicity reasons, the suture 4 is shown only in the last phase (d) of FIG. 1.

If the anchor shown in FIG. 1 is to be used in connection with a K-wire, the vibration tool 1 and the anchor foot 22 comprise an axial channel for accommodation of the K-wire, wherein this channel extends e.g. along the axis of the anchor foot and the eyelet 85 has an eccentric position.

If after fixation of the suture anchor 2, the suture 4 is still to be slideable relative to the anchor, the suture end portions extend preferably through the thermoplastic sleeve 23 or through the vibration tool 1, which for such purpose may comprise an axial channel at least through its distal end portion. If the suture 4 is to be locked relative to the anchor together with the anchor being fixated, the suture end portions extend preferably on the outside of the thermoplastic sleeve 23, wherein, for preventing damage of the suture during the process of forcing the anchor foot 22 into the hard tissue, axial suture grooves (not shown) may be provided on the thermoplastic sleeve (see also FIG. 4). As illustrated in FIG. 1, the vibration tool 1 may reach through the whole length of the thermoplastic sleeve 23. Alternatively, the anchor foot 22 may reach into or through the thermoplastic sleeve 23 and possibly comprise the means for holding the suture (e.g. an eyelet) in such proximal region.

Phase (a) of FIG. 1 shows the suture anchor 2 mounted on the distal end of tool 1, the anchor foot 22 being connected to the distal tool end and the thermoplastic sleeve 23 sitting against the proximal face of the anchor foot 22 (or being attached thereto, see FIG. 4) and surrounding the distal tool end (or a proximal anchor foot part) loosely. The connection between the anchor foot 22 and the distal tool end is such that it can transmit a force directed into the hard tissue (pushing force or compressive force) as well as a force directed away from the hard tissue (pulling force or tensile force) to the anchor foot 22, such that vibration is transmitted from the tool to the anchor foot, and such that the tool 1 can be easily disconnected from the anchor foot 22 after completion of the fixation process. Suitable connections are e.g. a bayonet coupling, cooperating inner and outer threads or possibly a predetermined breaking point suitable for being broken by rotation of the tool relative to the anchor. Such connections without axial play are able to fully transmit the vibration. Such connections with axial play, in particular bayonet connections with axial play, are possible also but will transmit only half of the vibration wave (hammering effect in the forcing step). If the connection is designed for being able to transmit a rotational force from the tool 1 into the anchor foot 22, the forcing process may be enhanced not only by vibration but also by rotation of the anchor foot 22.

In addition to the anchor 2 (anchor foot 22 and thermoplastic sleeve 23) and the vibration tool 1, the device for carrying out the method according to FIG. 1 further comprises a support element 80 with a tube-shaped part 81 fitting into the opening 5.1 and allowing the distal tool end to reach through it. The cross section of the tube-shaped part 81 is the same or preferably somewhat smaller than the cross section of the anchor foot 22 such that it is capable of being introduced with no, or hardly any force into the hard tissue opening produced by forcing the anchor foot into the hard tissue. The support element 80 preferably further comprises a flange-shaped part 82 allowing the support element to sit on the hard tissue surface with the tube-shaped part 81 extending into the opening 5.1. The support element may be part of a guide tool (not shown) for guiding the vibration tool and being attached to the vibration source (not shown) to which the proximal end of the vibration tool is coupled or to a housing thereof. For a sub-cortical anchorage (or any anchorage in a predefined depth below a hard tissue surface) of the suture anchor 2 the tube-shaped part 81 of the support element 80 has an axial length which corresponds approximately with the thickness of the cortical bone layer 7 (or the predefined depth). For anchorage in other depths of the hard tissue, the tube-shaped part 81 may be longer or shorter or may be substantially absent (see FIG. 2). For leaving it to the surgeon to determine an optimal depth for the anchorage, the support element 80 may not comprise a flange-shaped part 82 or the latter may be constituted by a ring whose axial position on the tube-shaped part 81 can be adapted by the surgeon.

Phase (b) shows the suture anchor after having been forced into the cancellous bone 8 by applying the pushing force F.1 and preferably vibration V to the vibration tool 1, wherein the used vibration may be, as discussed further above, a vibration mode comprising amplitude modulation or pulses. During the forcing step, liquefaction of the material of the thermoplastic sleeve is prevented by using such a vibration mode, but can also be prevented by taking care that the thermoplastic sleeve 23 is not clamped between the support element 80 and the anchor foot 22. The anchor foot 22 has reached a sufficient depth in the cancellous bone when the flange-shaped part 82 of the support element 80 is able to be brought into contact with the hard tissue surface 6.

Phase (c) shows the anchor after the anchoring step which is effected by vibrating the tool 1 (vibration V, if applicable of a different vibration mode than used in the forcing step, base vibration) and applying the pulling force F.2 to it and by counteracting the pulling force F.2 by holding the support element 80 (or a corresponding guide tool, the support element being a part thereof) against the hard tissue surface (force F.3), i.e. applying a compressing force to the thermoplastic sleeve 23 or clamping it between anchor foot 22 and support element 80 respectively. Due to the thermoplastic sleeve 23 being such clamped between the anchor foot 22 and the support element 80 and due to the vibration, the material of the thermoplastic sleeve is at least partly liquefied starting from its proximal and/or distal face, depending e.g. on energy directors being provided to act on these end faces of the thermoplastic sleeve 23, and the liquefied material penetrates the hard tissue surrounding the thermoplastic sleeve 23. With the thermoplastic sleeve getting shorter through liquefaction and displacement of the sleeve material, the support element 80 remains held against the hard tissue surface and the anchor foot 22 is moved in the hard tissue in a direction against the hard tissue surface, leaving void the bottom 5.2 of the opening 5 which was established or at least enlarged in the forcing step.

Phase (d) shows the suture anchor 2 finally fixated, the tool 1 disconnected from the anchor foot 22 and tool 1 and support element 80 being removed from the fixation site.

Of course it is possible also to not remove the support element 80 after completion of the anchoring step, wherein it is advantages to pair the materials of the support element 80 or at least a distal portion of it and the thermoplastic sleeve 23 or contact surfaces thereof, such that during the anchoring step the support element 80 is fastened to the thermoplastic sleeve 23 by being welded or adhered thereto or by a positive fit connection between the two. The support element remaining in the fixation site may serve for safeguarding the suture 4 from being damaged by the edge of cortical bone or other hard tissue at the mouth of the bone opening 5.1 on tensioning the suture e.g. along the bone surface 6.

Anchorage with the aid of the in situ liquefaction of the material having thermoplastic properties is very little dependent on the quality of the hard tissue, which in an embodiment according to FIG. 1 may even be completely absent (soft tissue or body cavity below the cortical bone layer). In the latter case, the liquefied material may or may not penetrate the inner surface of the cortical bone layer and be held in the hard tissue opening 5.1 mainly by the fact of constituting after re-solidification a body which cannot pass through the opening any more. This means that the fixation according to the invention is suitable not only for a subcortical fixation in cancellous bone of a reduced mechanical stability but also in absence of cancellous bone e.g. in the medullary cavity of long bones or on a non-accessible side of or beyond a bone plate (fixation by supra-cortical button).

Exemplary applications of supra-cortical buttons as mentioned above are e.g. regarding the human shoulder: acute acromioclavicular joint stabilization; and regarding the human foot: fixation of syndesmosis disruptions. In the named applications, the suture fixated by the supra-cortical button may be a suture bundle which is used to directly replace a tendon or ligament.

As described in the cited publication WO 2009/109057, it may be advantageous to equip the device as shown in FIG. 1 for a more automated method by providing a pre-tensioned resilient element (e.g. pre-tensioned spring) arranged to connect the tool 1, the anchor 2 and the support element 80 (or a corresponding guide tool) to form a closed load frame, the resilient element and its pre-tensioning being dimensioned for supplying the clamping force for clamping the thermoplastic sleeve 23 between the anchor foot 22 and the support element 80 and to drive the relative axial movement between the anchor foot 22 and the support element 80 when the thermoplastic sleeve 23 gets shorter.

FIG. 2 illustrates a further exemplary embodiment of the method according to the invention, wherein the device (vibration tool 1, anchor foot 22, thermoplastic sleeve 23 and support element 80) is shown after completion of the forcing and anchoring steps but before removal of the tool 1 and the support element 80. The method illustrated in FIG. 2 differs from the method illustrated in FIG. 1 only in that it does not result with the proximal face of the thermoplastic sleeve 23 positioned at a predetermined depth below the hard tissue surface (e.g. approximately at the inner surface of the cortical bone layer, but in an anchor fixation in which the proximal face of the thermoplastic sleeve is finally about flush with the bone surface 6. Such anchorage is achieved by using a support element 80 with substantially no tube-shaped part and preferably by controlling the anchoring step such that the material of the thermoplastic sleeve 23 is mainly liquefied starting from the distal end thereof. The suture, which is not shown in FIG. 2 extends preferably through the thermoplastic sleeve 23 and the support element 80 and is therewith safeguarded against damage through friction on the bone of the mouth of the bone opening by the thermoplastic sleeve 23.

FIGS. 3 to 6 show further exemplified embodiments of anchors or devices comprising anchor 2, tool 1 and possibly support element 80, which devices are suitable for the methods as illustrated in FIG. 1 or 2, wherein the features of these anchors and devices and of the anchor and device shown in FIGS. 1 and 2 can also be used in combinations different from the shown combinations.

The device according to FIG. 3 is equipped for liquefaction of the material of the thermoplastic sleeve 23 starting from the proximal sleeve face as preferred in the method according to FIG. 1. This is effected by the distal face of the support element 80 tapering to a relatively sharp inner edge 83, the sharp edge serving as energy director and the taper enhancing the displacement of the liquefied material radially outwards and into the bone wall of the bone opening. Liquefaction at the distal face of the thermoplastic sleeve may be prevented by not providing energy directors there (contact area between anchor foot 22 and thermoplastic sleeve 23 as large and as even as possible) and/or by fastening the thermoplastic sleeve 23 to the anchor foot 22. This can be achieved e.g. as illustrated in FIG. 3 by a distal end of the thermoplastic sleeve 23 sitting in a corresponding bush of the anchor foot 22 and being retained therein e.g. by a force fit or friction fit. The same effect may also be achieved by e.g. gluing, welding or screwing the two anchor parts together or by manufacturing the anchor foot 22 and the thermoplastic sleeve 23 as one piece (see also FIG. 4), e.g. from the same material which, in the region of the distal anchor foot end, may be strengthened for the forcing step by a suitable filler or a metal insert.

FIG. 3 further shows the vibration tool equipped with a stop 1.1 for limiting the depth to which the anchor foot can be forced into the bone tissue. This stop 1.1. is e.g. constituted by a step separating a distal tool portion with a cross section adapted to the axial channel of the thermoplastic sleeve 23 from a proximal tool portion with a larger cross section not able to be introduced into the thermoplastic sleeve. Therein, for preventing undesired liquefaction of the thermoplastic sleeve 23 at the end of the forcing step, care is to be taken to dimension the axial length of the distal tool portion such, that there is enough room between the stop 1.1 and the anchor foot 22 for the thermoplastic sleeve in its original maximum length to be able to sit loosely between the anchor foot 22 and the support element 80. In addition to the named measure for preventing undesired liquefaction during the forcing step or instead of it, the vibration mode for the forcing step can be chosen accordingly, as discussed further above.

As above mentioned for the device according to FIG. 2 also the anchor according to FIG. 3 (or any other anchor described further below) may comprise an axial channel for accommodation of a K-wire, wherein the anchor needs to be designed such that on threading the anchor along the K-wire the wire does not interfere with the suture being threaded through the anchor foot or extending therefrom.

FIG. 4 shows a one-piece anchor 2 with portions constituting anchor foot 22 and thermoplastic sleeve 23. A loop of the suture 4 is retained in an eyelet 85 (or other suitable system of passages and/or grooves) provided in the anchor foot portion 22. For safeguarding the suture 4 from getting damaged when the anchor is forced into the hard tissue and/or from getting damaged during the anchoring step through the vibration or the liquefied material, axial suture grooves 86 may be provided in the thermoplastic sleeve portion 23. The anchor according to FIG. 4 may be made of only one material e.g. of a suitably filled polylactide material, wherein the anchor foot portion 22 may be filled to a higher degree than the thermoplastic sleeve portion 23. Alternatively the anchor foot portion is made of a different material suitable for the forcing step (for examples see further above) than the material having thermoplastic properties of the thermoplastic sleeve portion. The arrangement of the suture 4 may make it possible for the suture to remain slideable relative to the anchor during the forcing and possibly after the anchoring step or for locking the suture relative to the anchor during the anchoring step.

FIG. 5 shows an anchor foot 22 which, for retaining the suture 4, comprises an eyelet 85 and a pair of axial suture grooves 86 extending from the eyelet to the proximal face of the anchor foot (system of passages and/or grooves) from where the suture 4 may extend inside the thermoplastic sleeve (not shown) or along its outer surface where suture grooves may be provided (as shown in FIG. 4) or not. For attachment to a distal tool end, the anchor foot 22 according to FIG. 5 comprises a threaded post adapted to a corresponding inner thread provided on the distal tool face (not shown).

FIG. 6 shows an anchor 2 equipped for retaining a suture knot 4.1 in a recess provided at an entrance to the eyelet 85, the suture 4 extending from the suture knot 4.1 through the eyelet 85, in a suture groove 86 to the proximal face of the anchor foot 22 and then along a slot 87 (or groove) extending from the distal to the proximal face of the thermoplastic sleeve 23. Any other per se known method for retaining the suture in the anchor foot is applicable for the invention.

Figure 7:
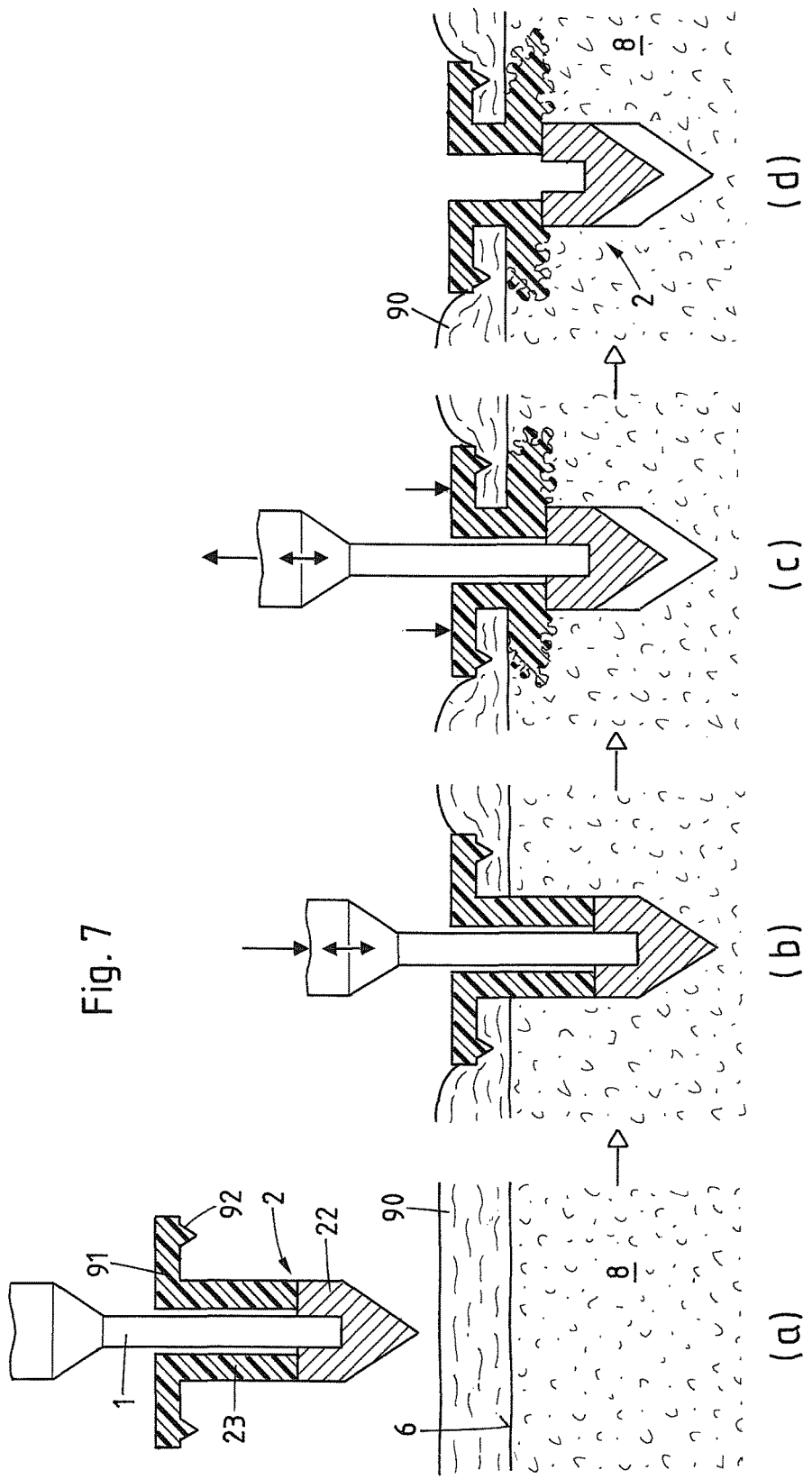
FIG. 7 illustrates a further exemplary embodiment of the method according to the invention, wherein the anchor is a headed anchor for fixating e.g. soft tissue and wherein the thermoplastic sleeve is liquefied preferably starting at its distal end.

FIG. 7 illustrates a further exemplary embodiment of the method according to the invention with four consecutive phases (a) to (d) of a fixation of a headed anchor 2, wherein the headed anchor is e.g. suitable for being used for fixating a soft tissue 90 (e.g. ligament or tendon) or a corresponding prosthetic element to hard tissue (e.g. bone). The soft tissue 90 is illustrated to be fixated to bone tissue which e.g. does not have a cortical layer (decorticated bone tissue, i.e. substantially cancellous bone tissue 8 only) or has a cortical layer through which the headed anchor can be forced, the distal anchor end e.g. being shaped like a bone awl. The anchor 2 again comprises an anchor foot 22 equipped for the forcing step as described further above in connection with FIGS. 1 to 6 and a thermoplastic sleeve 23, wherein the thermoplastic sleeve 23 carries a flange-shaped proximal portion constituting the anchor head 91 and further constituting an equivalent to the flange-shaped part of the support element according to FIG. 1 in the anchoring step. The anchor head 91 is preferably made of the same material as the thermoplastic sleeve 23 but may also be made of a different material. The anchor head 91 may, in a per se known manner, comprise distal protrusions 92 which are pressed into the soft tissue 90 during the fixation process.

The four phases (a) to (d) shown in FIG. 7 are substantially the same as the four phases (a) to (d) shown in FIG. 1 and are therefore only commented below as far as they differ from the latter.

In phase (b), the anchor 2 is shown when forced into the hard tissue to a sufficient depth which is achieved when the anchor head 91 is able to press the soft tissue 90 against the bone surface 6 and the soft tissue 90 is compressed such that the distal protrusions 92 of the anchor head 91 are pressed into the soft tissue or even through it and possibly into the bone surface 6. Phase (d) shows the headed anchor 2 finally anchored in the cancellous bone tissue 8 and the soft tissue 90 therewith safely attached to the bone tissue.

Figure 8:
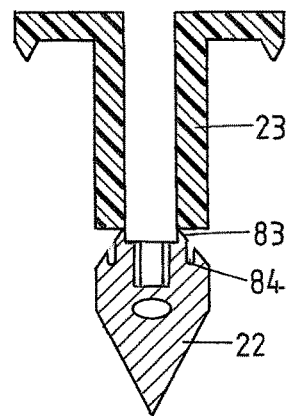
FIG. 8 shows a preferred detail of the anchor illustrated in FIG. 7.

If the anchor 2 according to FIG. 7 comprises means for retaining a suture as illustrated in the previous Figs. and in FIG. 8, it can of course also be used for fixating a suture relative to bone tissue instead of for fixating a soft tissue relative to bone tissue.

In the embodiment of the method according to the invention as illustrated in FIG. 7 it is necessary, in the embodiment as illustrated in FIG. 2 it is preferred that the liquefaction process starts at the distal end of the thermoplastic sleeve and therefore it is advantageous to equip the contact area between the distal face of the thermoplastic sleeve 23 and the proximal face of the anchor foot 22 with energy directors. FIG. 8 shows a preferred embodiment of such energy directors which have the form of the proximal face of the anchor foot 22 tapering inwards to form a relatively sharp edge 83 adapted to the cross section of the axial channel through the thermoplastic sleeve 23, wherein the relatively sharp edge 83 constitutes the energy directors and the taper enhances displacement of the liquefied material radially outward and therewith into the bone tissue surrounding the anchor (re-enforcement or augmentation of the tissue which finally surrounds the anchor foot). Furthermore, FIG. 8 shows recesses, preferably undercut recesses, arranged in the tapering proximal face of the anchor foot 22, which, during the anchoring step, will be filled with the liquefied material to connect the anchor foot 22 to the thermoplastic sleeve 23 in a positive-fit connection in the finally fixated anchor. As is further illustrated in FIG. 9, phase (c), which shows a similar anchor in an anchored configuration, the named design of the proximal anchor foot face further helps to stabilize the anchor foot against loads which act at an angle to the anchor axis and which, especially in hard tissue of little mechanical resistance, may otherwise be able to tilt or laterally dislocate the anchor foot.

Figure 9:
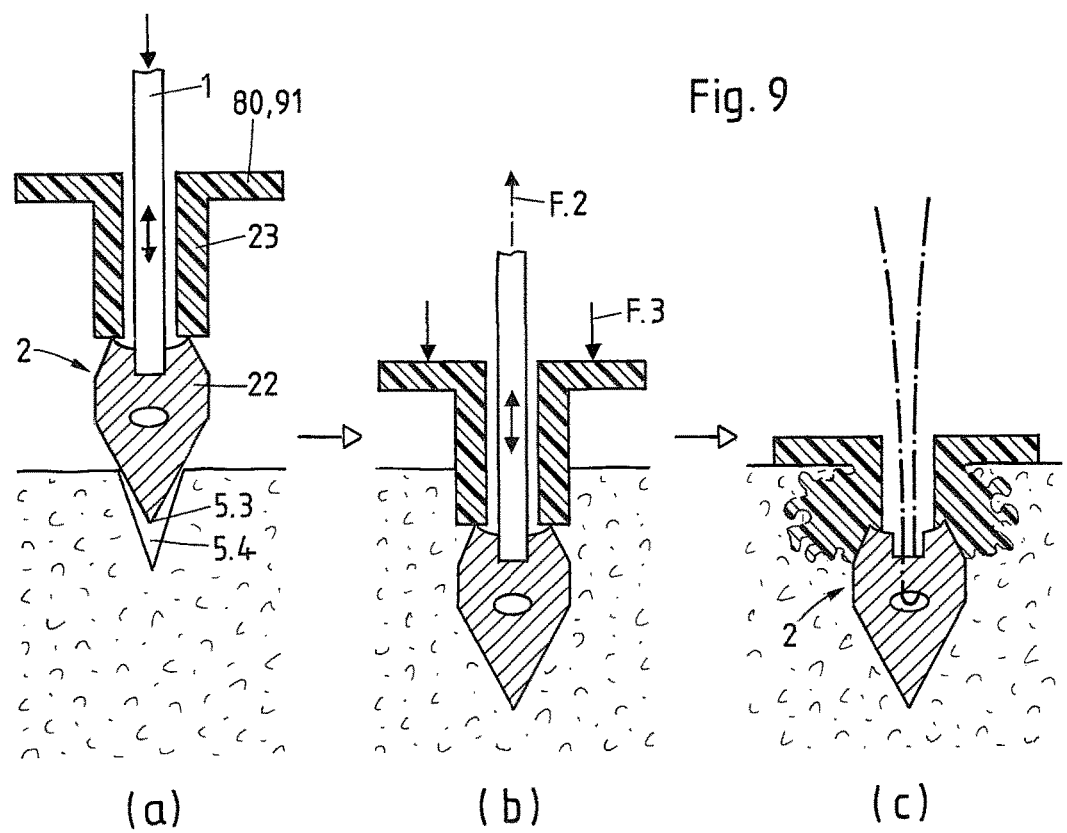
FIG. 9 illustrates a further exemplary embodiment of the method according to the invention, wherein the anchor foot is stationary relative to the bone tissue during the anchoring step.

FIG. 9 illustrates a further exemplary embodiment of the method according to the invention, wherein the anchor may be of a similar kind as the anchor according to FIG. 8 (suture only shown in phase (c)) and may comprise a head or none, or may be a headed anchor. As described further above, the anchor foot is forced into the bone tissue in the forcing step and remains in the same position during the anchoring step, the material of the thermoplastic sleeve preferably being liquefied starting from the distal end of the thermoplastic sleeve and, depending on the anchor design, the support element 80 or the anchor head 91 being moved towards the stationary anchor foot 22 and the force F.3 used for such movement being counteracted preferably by the tensile force F.2 applied to the vibration tool 1 and/or possibly by the bone tissue in contact with the distal face of the anchor foot.

FIG. 9 shows the method in three consecutive phases (a) to (c). Phase (a) shows the device for carrying the method positioned in a pilot bore 5.4 being provided in the bone tissue. The same as described above for the other embodiments of the invention, the anchor 2 comprises an anchor foot 22 suitable for being forced into hard tissue and a thermoplastic sleeve 23, wherein the thermoplastic sleeve 23 may comprise a flange-shaped proximal portion (anchor head 91) or the device further comprises a support element 80. The anchor foot 22 is fastened to the distal end of the vibration tool 1 and the thermoplastic sleeve 23 sits loosely on the proximal face of the anchor foot 22. Phase (b) shows the anchor after the forcing step in which the anchor is forced into the pilot bore 5.4 with the aid of a pushing force F.1 acting through the vibration tool 1 on the anchor foot 22, whereby the pilot bore 5.4 is enlarged regarding cross section and/or depth. As also shown in phase (b), in the anchoring step, the anchor head 91 or the support element 80 is moved towards the anchor foot 22 with the aid of force F.3 which is applied to the anchor head or the support element and which is counteracted by the pulling force F.2 acting on vibration tool 1 and/or by the bone tissue in the area of the distal face of the anchor foot, wherein these forces are dimensioned such that the anchor foot remains substantially stationary relative to the bone tissue. Phase (c) shows the fixated anchor after completion of the forcing step and the anchoring step and after removal of the vibration tool 1.

Figure 10:
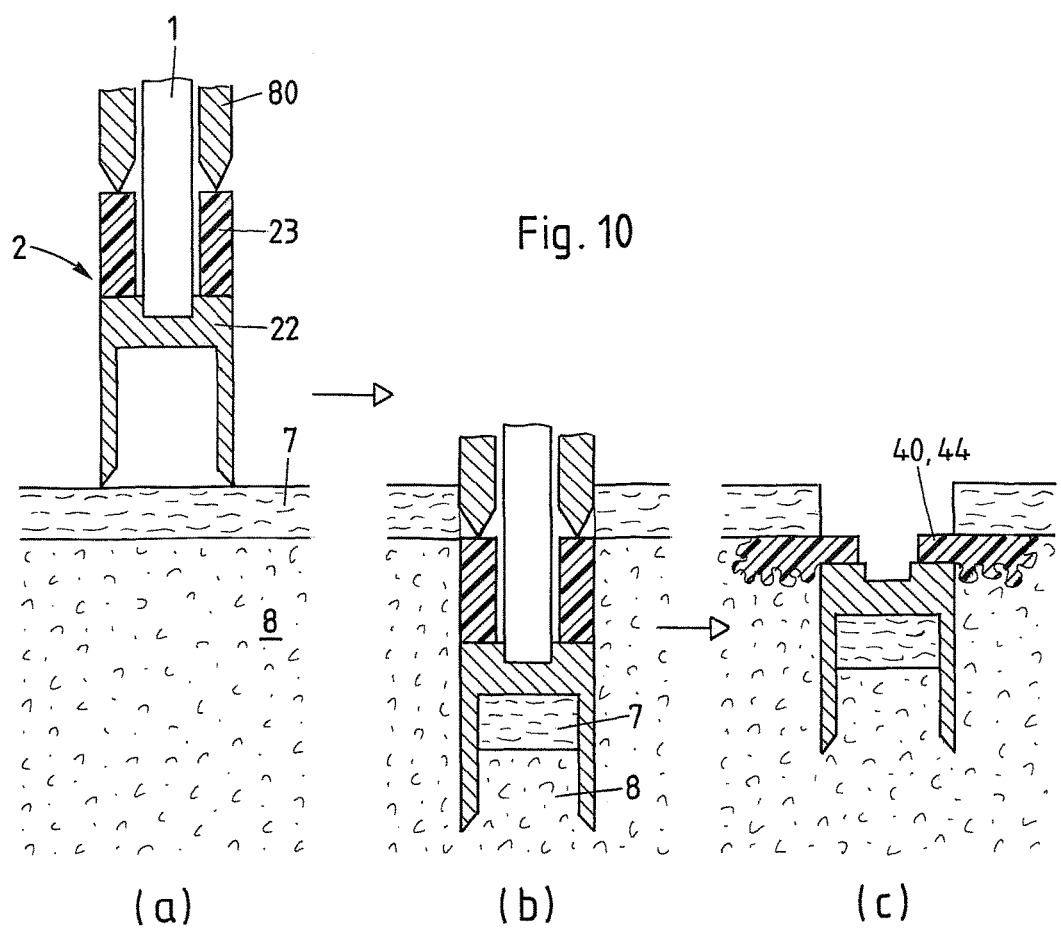
FIG. 10 shows a further exemplary embodiment of an anchor applicable in the method according to the invention.

FIG. 10 shows an anchor 2 suitable for the method according to the invention, the anchor comprising an anchor foot 22 which is equipped for being forced into hard tissue by punching through the hard tissue, the punching process preferably being assisted with vibrational energy coupled into the anchor foot 22 as above described. The anchor foot as shown in FIG. 10 is suitable for all embodiments of the method according to the invention as described above. It is particularly suited for being forced through a cortical bone layer 7 into tissue underneath the cortical bone layer which can be compacted to accommodate the punched-out piece of the cortical bone layer (e.g. cancellous bone tissue 8) or into a cavity or soft tissue underneath the cortical bone layer 7. FIG. 10 shows a method embodiment similar to the method illustrated in FIG. 1, wherein the anchor foot 22 is shown positioned for the punching step (phase (a)), between the punching step and the anchoring step (phase (b)) and after the anchoring step (phase (c)). The anchor foot 22 according to FIG. 10 can be used in combination with any system of passages and/or grooves for retaining a suture and/or in a headed anchor as described above.

The anchor foot 22 according to FIG. 10 comprises a distal end in the form of a hollow cylinder (circular or non-circular) having a thin wall and a sharpened distal face, is mounted for the punching (forcing step) and for the anchoring step on the distal end of the vibration tool 1, wherein the thermoplastic sleeve 23 sits between the anchor foot 22 and a counter element 80. For the punching step, the anchor foot 22 is positioned e.g. on the cortical bone layer 7 in the location in which a sub-cortical fixation of the anchor foot 22 is to be achieved (phase (a)). With the aid of the tool 1 and vibration transmitted through the tool 1 into the anchor foot 22, the anchor foot 22 is forced into the bone tissue punching out a piece thereof and displacing it further into the cancellous bone tissue 8 situated underneath the cortical bone layer 7 and at the same time compacting the cancellous bone tissue 8 (phase (b)). The anchor foot 22 has reached a sufficient depth in the bone tissue, when the liquefaction location (e.g. the interface between the distal face of the counter element 80 and the proximal face of the thermoplastic sleeve 23) has passed the cortical bone layer 7. As soon as the anchor has reached this final position, the force acting on the tool 1 is reversed (from pushing to pulling action) and while the thermoplastic sleeve 23 is at least partly liquefied, the anchor foot 22 is pulled against the cortical bone layer, the liquefied sleeve material anchoring the anchor foot 22 on the inside of the cortical bone layer 7 (re-solidified material 40) or forming a body 44 which cannot pass the opening punched through the cortical bone layer.

The above described embodiments of the invention concern, in particular, suture anchors suitable for soft tissue attachment to hard tissue. In all the described embodiments of methods for fixating such suture anchors in hard tissue the sutures may be safeguarded against damage by heat dissipating from the material having thermoplastic properties when liquefied, by being soaked with liquid (water or saline solution) preferably before being threaded through the suture anchor or a part thereof or before being positioned in the hard tissue opening and necessarily before liquefaction of the material having thermoplastic properties.

In the above description a plurality of embodiments of the invention are described having specific features. One skilled in the art and having knowledge of the above description will easily be able to adapt suitable ones of these features for other ones of the embodiments and add them to these other embodiments or use them for replacing features described for these other embodiments. In the same way, one skilled in the art and knowing the above description will easily be able to make suitable combinations of suitable ones of the illustrated and described embodiments of the invention.

What is claimed is:

1. An suture anchor equipped for being anchored in hard tissue with the aid of in situ liquefaction of a material having thermoplastic properties,
the anchor comprising a proximal anchor part and a distal end portion, said proximal anchor part being formed from the material having thermoplastic properties, said distal end portion being equipped for being forced into or through hard tissue,
wherein the anchor is a one piece anchor; and
wherein the anchor distal end portion is directly connectable to a tool via a connection that is capable of transmitting an axial compressive force as well as mechanical vibrations to the proximal anchor part,
wherein the anchor comprises a system of passages and/or grooves for holding at least one suture, and
wherein the material having thermoplastic properties of the proximal anchor part is liquefied by a combined action of the axial compressive force and the mechanical vibration to yield liquefied material, whereby said the liquefied material is laterally displaced while an axial dimension of the anchor is simultaneously reduced.

2. The anchor according to claim 1, wherein the distal end portion of the anchor serves as a tip.

3. The anchor according to claim 1, wherein the distal end portion of the anchor serves as a punching tool.

4. The anchor according to claim 1, wherein the system of passages or grooves includes at least one eyelet.

5. A device for anchoring a suture in hard tissue with the aid of in situ liquefaction of a material having thermoplastic properties, the device comprising:
   the anchor, a tool, and a support element,
   wherein the anchor comprises the material having thermoplastic properties and a distal end portion that is equipped for being forced into or through hard tissue, the anchor being a one piece anchor and having a system of passages and/or grooves for holding at least one suture,
   wherein the anchor material having thermoplastic properties is liquefied by a combined action of the axial compressive force and the mechanical vibration to yield liquefied material, whereby said the liquefied material is laterally displaced while an axial dimension of the anchor is simultaneously reduced;
   wherein the tool has a distal end that is connected or connectable to the anchor by the connection,
   wherein the connection between the distal end of the tool and the anchor
     is capable of being disconnected and
     is adapted to transmit the axial compressive force well as mechanical vibration from the tool to the anchor; and
   support element sits on a proximal face of the anchor with the tool extending through the support element.

6. The device according to claim 5 and further comprising a vibration source, a proximal end of the tool being coupled or couplable to the vibration source.

7. The device according to claim 6, wherein the vibration source is capable of selectively producing two different vibration modes.

8. The device according to claim 7, wherein a first one of the two different vibration modes is selected from the group consisting of amplitude modulated and pulsed.

9. A surgical device comprising:
   an anchor comprising a material having thermoplastic properties for in situ liquefaction of the material having thermoplastic properties and
   a tool,
   wherein the anchor comprises an anchor piece with a distal end portion being equipped to be forced into or through hard tissue, and
   wherein the tool extends through the material having thermoplastic properties and has a distal end that is directly connected to the anchor piece, wherein the direct connection provides physical contact between the distal end of the tool and the anchor piece, and
   wherein the direct connection between the distal end of the tool and the anchor piece
   is capable of being disconnected and
   is adapted to transmit an axial compressive force as well as mechanical vibration from the tool to the anchor piece
   wherein the anchor material having thermoplastic properties is adapted to be liquefied by combined action of the axial compressive force and the mechanical vibration, to yield liquefied material, whereby said the liquefied material is laterally displaced while an axial dimension of the anchor is simultaneously reduced.

10. The device according to claim 9, further comprising a vibration source, a proximal end of the tool being coupled or couplable to the vibration source.

11. The device according to claim 10, wherein the vibration source is capable of selectively producing two different vibration modes.

12. The device according to claim 11, wherein a first one of the two different vibration modes is selected from the group consisting of amplitude modulated and pulsed.

13. The device according to claim 9, wherein the anchor is a headed anchor adapted to fix a soft tissue to hard tissue, wherein the headed anchor comprises an anchor head with a proximal flange, wherein the flange comprises a distal clamping face that is adapted to clamp a soft tissue between the anchor head and hard tissue.

14. The device according to claim 13, wherein the anchor head comprises distal protrusions at the flange that are adapted for pressed into the soft tissue in a fixed state of the headed anchor.

15. The device according to claim 13, wherein the headed anchor comprises a system of passages and/or groove, wherein the system is configured to hold a loop of at least one suture.

16. The device according to claim 9, wherein the anchor is a suture anchor comprising a system of passages and/or groove, wherein the system is configured to hold a loop of at least one suture.

17. The device according to claim 16, wherein the system is constituted by at least one eyelet.

18. The device according to claim 16, wherein the anchor comprises at least one axial suture groove for accommodation of the at least one suture.

* * * * *